US011529204B2

(12) United States Patent
Maki et al.

(10) Patent No.: US 11,529,204 B2
(45) Date of Patent: Dec. 20, 2022

(54) SUPPORT SYSTEM, SUPPORT METHOD, AND SUPPORT PROGRAM

(71) Applicant: TERUMO KABUSHIKI KAISHA, Tokyo (JP)

(72) Inventors: Toshio Maki, Shizuoka (JP); Yoshiyuki Hara, Shizuoka (JP); Osamu Nomura, Shizuoka (JP); Yuuki Sakaguchi, Shizuoka (JP); Yuusuke Sekine, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 391 days.

(21) Appl. No.: 16/887,041

(22) Filed: May 29, 2020

(65) Prior Publication Data
US 2020/0289215 A1 Sep. 17, 2020

Related U.S. Application Data

(63) Continuation of application No. PCT/JP2018/028729, filed on Jul. 31, 2018.

(30) Foreign Application Priority Data

Nov. 30, 2017 (JP) .............................. JP2017-230859

(51) Int. Cl.
*A61B 34/32* (2016.01)
*A61B 34/10* (2016.01)
(Continued)

(52) U.S. Cl.
CPC .............. *A61B 34/32* (2016.02); *A61B 34/10* (2016.02); *A61B 34/25* (2016.02); *G06N 20/00* (2019.01);
(Continued)

(58) Field of Classification Search
CPC ......... A61B 34/32; A61B 34/10; A61B 34/25; A61B 2034/254; A61B 2034/256;
(Continued)

(56) References Cited

U.S. PATENT DOCUMENTS 9,788,907 B1 10/2017 Alvi et al.
2004/0230094 A1 11/2004 Nakamura
(Continued)

FOREIGN PATENT DOCUMENTS

CN 107077385 * 8/2017 ............. G06F 9/485
JP H11197159 A 7/1999
(Continued)

OTHER PUBLICATIONS

An English Translation of the International Search Report (Form PCT/ISA/210) and the Written Opinion of the International Searching Authority (Form PCT/ISA/237) dated Oct. 9, 2018, by the Japanese Patent Office in corresponding International Application No. PCT/JP2018/028729. (7 pages).
(Continued)

*Primary Examiner* — Jerome Grant, II
(74) *Attorney, Agent, or Firm* — Buchanan Ingersoll & Rooney PC

(57) ABSTRACT

A support system, a support method, and a support program in the form of a non-transitory computer readable medium are disclosed that support a medical action during an operation. The support system includes a data acquisition unit configured to acquire, during an operation, use state data on a use state of a medical device during the operation, and target lesion data on a target lesion of a patient during the operation, a learning unit configured to perform machine learning using the use state data and the target lesion data, and a presentation unit configured to present a recommended operation policy based on a result of the machine learning.

20 Claims, 6 Drawing Sheets

(51) Int. Cl.
  *A61B 34/00* (2016.01)
  *G06N 20/00* (2019.01)
  *A61B 34/30* (2016.01)
(52) U.S. Cl.
  CPC ... *A61B 2034/254* (2016.02); *A61B 2034/256* (2016.02); *A61B 2034/303* (2016.02)
(58) Field of Classification Search
  CPC .... A61B 2034/303; G06N 20/00; G06N 3/08; G16H 20/40; G16H 30/20; G16H 40/20; G16H 50/20; G16H 40/63
  USPC ........................................................ 606/130
  See application file for complete search history.

(56) References Cited

U.S. PATENT DOCUMENTS

| | | |
|---|---|---|
| 2006/0253296 A1 | 11/2006 | Liisberg et al. |
| 2014/0081659 A1 | 3/2014 | Nawana et al. |
| 2016/0259888 A1 | 9/2016 | Liu et al. |
| 2017/0360508 A1* | 12/2017 | Germain ................ G16H 50/50 |
| 2018/0056938 A1* | 3/2018 | Shin ........................ E05F 15/79 |
| 2018/0122067 A1* | 5/2018 | Reicher ................... A61B 6/463 |
| 2021/0174957 A1* | 6/2021 | Lebedev ............. A61B 5/7267 |

FOREIGN PATENT DOCUMENTS

| | | |
|---|---|---|
| JP | 2004181229 A | 7/2004 |
| JP | 2007512588 A | 5/2007 |
| JP | 2015531661 A | 11/2015 |
| WO | 2016140795 A1 | 9/2016 |

OTHER PUBLICATIONS

International Search Report (with English Translation) and Written Opinion issued in corresponding International Patent Application No. PCT/JP2018/028729, 9 pages (dated Oct. 9, 2018).

* cited by examiner

| SAMPLING TIME | OPERATION POLICY | MEDICAL DEVICE IN USE | ELAPSED TIME | PROGRESS STATE |
|---|---|---|---|---|
| ××:×× | ○○○○ | △△△△ | ○○:○○ | □□□□ |
| ××:×× | □□□□ | △△△△ | ○○:○○ | □□□□ |

| SAMPLING TIME | CONDITION OF TARGET LESION |
|---|---|
| ××:×× | DEGREE OF STENOSIS/ CHARACTERISTIC OF TARGET LESION |
| ××:×× | DEGREE OF STENOSIS/ |

| MEDICAL INSTITUTION NAME | DOCTOR NAME | PATIENT NAME | | | |
|---|---|---|---|---|---|
| A | O | S | ×××× | ×××× | ×××× |
| A | P | T | ×××× | ×××× | ×××× |
| B | Q | U | ×××× | ×××× | ×××× |
| A | R | V | ×××× | ×××× | ×××× |

| IDENTIFI- CATION ID | PATIENT NAME | STREET ADDRESS | AGE | OPERATION HISTORY | HEALTH CONDITION | TARGET LESION | CONDITION OF TARGET LESION |
|---|---|---|---|---|---|---|---|
| ××× | S | ××× | 25 | ELECTRONIC MEDICAL CHART | MEDICAL EXAMINATION RESULT, INQUIRY RESULT | CORONARY ARTERY | GOOD |
| ××× | T | ××× | 45 | ELECTRONIC MEDICAL CHART | MEDICAL EXAMINATION RESULT, INQUIRY RESULT | FEMORAL VEIN | NORMAL |
| ××× | U | ××× | 33 | ELECTRONIC MEDICAL CHART | MEDICAL EXAMINATION RESULT, INQUIRY RESULT | CEREBRAL ARTERY | NORMAL |
| ××× | V | ××× | 8 | ELECTRONIC MEDICAL CHART | MEDICAL EXAMINATION RESULT, INQUIRY RESULT | CORONARY ARTERY | GOOD |

| MEDICAL INSTITUTION NAME | ADDRESS | MEDICAL DEPARTMENT | BED | AMBU-LANCE | MEDICAL DEVICE | CLINICAL PATH | POLICY |
|---|---|---|---|---|---|---|---|
| A | × × × | SURGERY, INTERNAL MEDICINE | 25 | 1 | × × × / × × × / × × × | SCHEDULE TABLE | × × × |
| B | × × × | OPHTHALMOLOGY | 0 | 0 | × × × / × × × / × × × | SCHEDULE TABLE | × × × |
| C | × × × | OTOLARYNGOLOGY | 0 | 0 | × × × / × × × / × × × | SCHEDULE TABLE | × × |
| D | × × × | OBSTETRICS | 50 | 1 | × × × / × × × / × × × | SCHEDULE TABLE | × × |

| IDENTIFI-CATION ID | PATIENT NAME | PRESCRIPTION HISTORY A | PRESCRIPTION HISTORY B |
|---|---|---|---|
| × × × | S | DATE AND TIME, TYPE, DOSE, DOSAGE FORM | DATE AND TIME, TYPE, DOSE, DOSAGE FORM |
| × × × | T | DATE AND TIME, TYPE, DOSE, DOSAGE FORM | DATE AND TIME, TYPE, DOSE, DOSAGE FORM |
| × × × | U | DATE AND TIME, TYPE, DOSE, DOSAGE FORM | DATE AND TIME, TYPE, DOSE, DOSAGE FORM |
| × × × | V | DATE AND TIME, TYPE, DOSE, DOSAGE FORM | DATE AND TIME, TYPE, DOSE, DOSAGE FORM |

| PLAN | INSURANCE COST | COST OF MEDICAL DEVICE |
|---|---|---|
| A | ¥・・・,・・・ | ¥・・・,・・・ |
| B | ¥・・・,・・・ | ¥・・・,・・・ |
| C | ¥・・・,・・・ | ¥・・・,・・・ |
| D | ¥・・・,・・・ | ¥・・・,・・・ |

SUPPORT SYSTEM, SUPPORT METHOD, AND SUPPORT PROGRAM

CROSS-REFERENCES TO RELATED APPLICATIONS

This application is a continuation of International Application No. PCT/JP2018/028729 filed on Jul. 31, 2018, which claims priority to Japanese Patent Application No. 2017-230859 filed on Nov. 30, 2017, the entire content of both of which is incorporated herein by reference.

FIELD OF THE DISCLOSURE

The present disclosure generally relates to a support system, a support method, and a support program.

BACKGROUND DISCUSSION

Treatment results of a treatment in a body lumen such as a blood vessel have been improved every year according to an increase in device types and development of operation and treatment policies. In recent years, an operation support system or the like capable of performing an operation on a patient by a remote operation at a place away from an operating room has been developed (for example, see Japanese Patent Application Publication No. 2004-181229).

In general, the treatment results of the operation can depend greatly on the experience of a surgeon. In particular, in a case of the operation with a relatively high degree of difficulty, the determination of how to proceed with the operation depends on decisions of the surgeon in many cases. In addition, for the operation with a relatively high degree of difficulty, it may be necessary to appropriately review (and change if necessary) an operation policy (treatment policy) during the operation depending on a condition of a target lesion and a progress state of the device. Therefore, it is very important to secure objectivity and validity of the decision made by the surgeon during the operation.

SUMMARY

A support system, a support method, and a support program for supporting a medical action during an operation are disclosed.

A support system is disclosed for supporting a medical action during an operation including a data acquisition unit configured to acquire, during an operation, use state data on a use state of a medical device during the operation, and target lesion data on a target lesion of a patient during the operation, a learning unit configured to perform machine learning using the use state data and the target lesion data, and a presentation unit configured to present a recommended operation policy based on a result of the machine learning.

A support method is disclosed for supporting a medical action during an operation including acquiring, during the operation, use state data on a use state of a medical device during the operation, and target lesion data on a target lesion of a patient during the operation, performing machine learning using the use state data and the target lesion data, and presenting a recommended operation policy based on a result of the machine learning.

A non-transitory computer readable medium (CRM) storing computer program code executed by a computer processor that executes a process of supporting a medical action during an operation is disclosed, the process comprising: acquiring, during the operation, use state data on a use state of a medical device during the operation, and target lesion data on a target lesion of a patient during the operation; performing machine learning using the use state data and the target lesion data; and presenting a recommended operation policy based on a result of the machine learning.

The present disclosure presents the recommended operation policy based on the result of the machine learning. Since a doctor can receive the presentation of the operation policy in real time during the operation, it is possible to adopt an objective and valid operation policy that does not depend only on the doctor's own decision.

BRIEF DESCRIPTION OF THE DRAWINGS

FIG. 4A is a diagram illustrating use state data of the support system according to the present embodiment disclosed here.

FIG. 4B is a diagram illustrating target lesion data of the support system according to the present embodiment disclosed here.

FIG. 4C is a diagram illustrating health care worker data of the support system according to the present embodiment disclosed here.

FIG. 4D is a diagram illustrating patient data of the support system according to the present embodiment disclosed here.

FIG. 4E is a diagram illustrating medical institution data of the support system according to the present embodiment disclosed here.

FIG. 4F is a diagram illustrating prescription data of the support system according to the present embodiment disclosed here.

FIG. 4G is a diagram illustrating medical cost data of the support system according to the present embodiment disclosed here.

DETAILED DESCRIPTION

Figure 1:
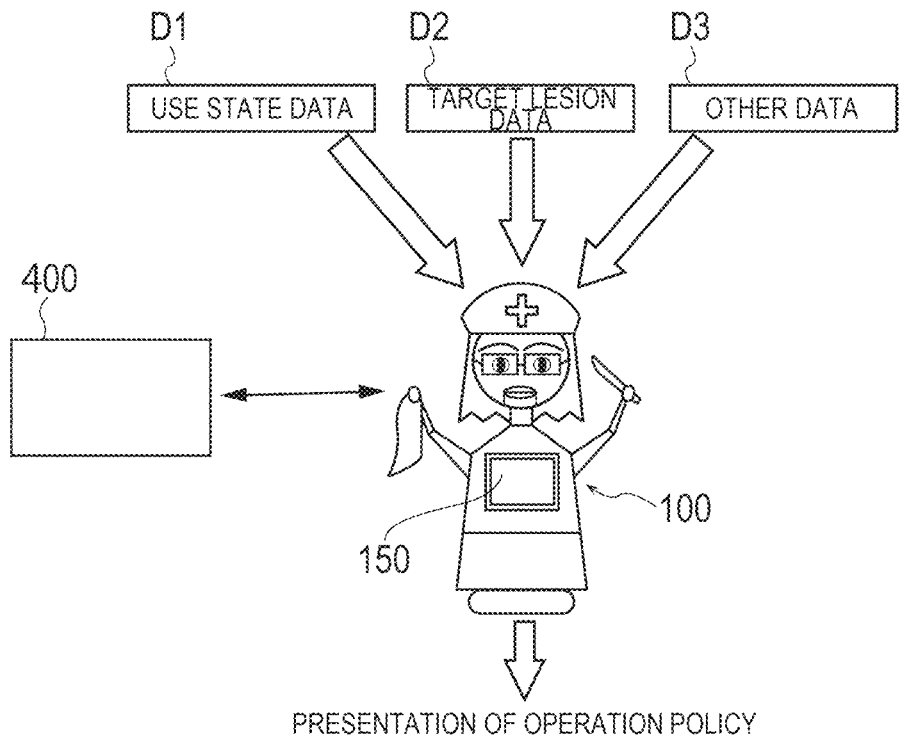
FIG. 1 is a diagram illustrating an outline of a support system according to an embodiment disclosed here.

Set forth below with reference to the accompanying drawings is a detailed description of embodiments of a support system, a support method, and a support program representing examples of the inventive support system, support method, and support program disclosed here. In the drawings, the identical elements are referenced by the identical symbols to avoid duplicative explanations. In addition, the dimensions in the drawings may be exaggerated for the sake of explanation and may differ from the actual dimensions.

Figure 2:
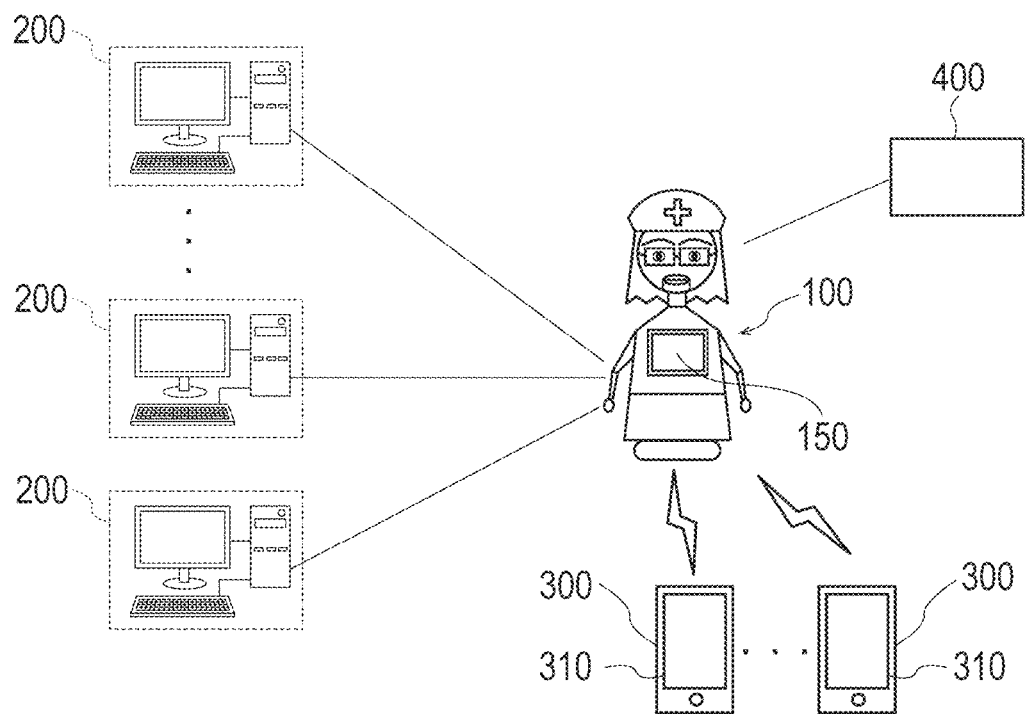
FIG. 2 is a diagram illustrating a network configuration of the support system according to the present embodiment disclosed here.
Figure 3A:
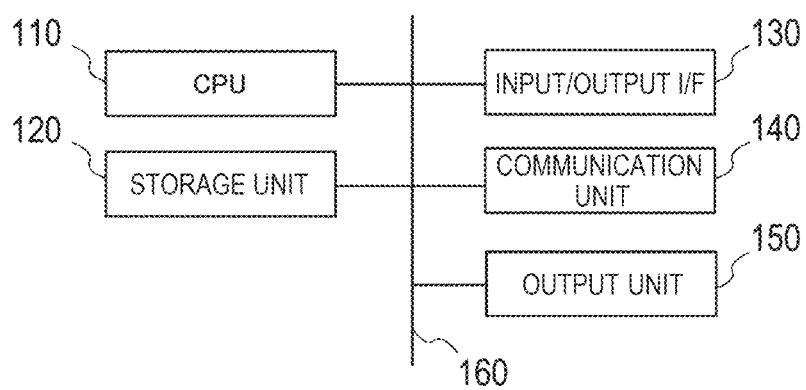
FIG. 3A is a block diagram illustrating a hardware configuration of the support system according to the present embodiment disclosed here.
Figure 3B:
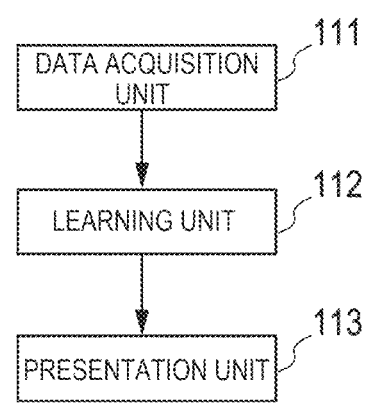
FIG. 3B is a block diagram illustrating a functional configuration of the support system according to the present embodiment disclosed here.

FIGS. 1 and 2 are diagrams for explaining an overall configuration of a support system 100 according to the present embodiment disclosed here. FIGS. 3A and 3B are diagrams for explaining each unit of the support system 100. FIGS. 4A to 4G are diagrams for explaining data handled by the support system 100.

As illustrated in FIG. 1, the support system 100 is a system for presenting an operation policy recommended in an operation using use state data D1, target lesion data D2, and other data D3 (health care worker data D31, patient data D32, medical institution data D33, prescription data D34, and medical cost data D35), and the like. In the present embodiment, although not particularly limited, the "medical institution" refers to, for example, a facility where a doctor performs an operation on a patient, and can include a hospital, a clinic, and the like. In addition, although not particularly limited, the "specific (constant) area" is, for example, an area divided by a municipality unit, a prefecture unit, or a country unit.

As illustrated in FIG. 2, the support system 100 is connected to medical institution terminals 200 of each medical institution and patient terminals 300 each owned by a patient via a network. The support system 100 is also connected to medical equipment (for example, a computed tomography (CT) apparatus, an operating table, a display monitor, or the like) 400 used during the operation via the network. The support system 100 has a function as a server that transmits and receives data to and from the medical institution terminal 200, the patient terminal 300, and the medical equipment 400.

The network can adopt, for example, a wireless communication method using a communication function such as WiFi® or Bluetooth®, other non-contact wireless communication, and wired communication.

In the present embodiment, the support system 100 is constituted by a working device capable of communicating with a person through interaction, holding, delivering, and handing an article or the like. For example, a robot equipped with an artificial intelligence (AI) program and an interactive function can be used as the working device. The working device can include an output unit 150 provided with a display capable of displaying a still image or a moving image and a speaker capable of outputting sound, music, and the like. Note that the working device can be equipped with a camera function capable of capturing the still image or the moving image. In addition, an appearance design of the working device is not particularly limited, and examples of the appearance design of the working device can include, for example, a human type and an animal type.

The working device can be constituted by, for example, a plurality of devices. In addition, the working device can be constituted as, for example, a program capable of executing by the central processing unit (CPU). In this case, the working device is not necessarily constituted as a robot-type device like the working device illustrated in FIG. 1, but can be constituted as one function of a control unit included in the support system 100 (server), that is, a form without a hardware such as a robot.

Hereinafter, the support system 100 will be described in detail.

The hardware configuration of the support system 100 will be described.

Although not particularly limited, the support system 100 can be constituted by, for example, a mainframe or a computer cluster. As illustrated in FIG. 3A, the support system 100 can include a central processing unit (CPU) 110, a storage unit 120, an input/output interface (input/output I/F) 130, a communication unit 140, and the output unit 150. The CPU 110, the storage unit 120, the input/output I/F 130, the communication unit 140, and the output unit 150 are connected to a bus 160, and transmit and receive data and the like to and from each other via the bus 160.

The CPU 110 is configured to execute control of each unit and various arithmetic processes according to various programs stored in the storage unit 120.

The storage unit 120 can include a read only memory (ROM) for storing various programs or various data, a random access memory (RAM) for temporarily storing programs or data as a work area, a hard disk for storing various programs or various data including an operating system (OS).

The input/output I/F 130 is an interface for connecting input devices such as a keyboard, a mouse, a scanner, and a microphone and output devices such as a display, a speaker, and a printer.

The communication unit 140 is an interface for communicating with the medical institution terminal 200, the patient terminal 300, and the medical equipment 400.

The output unit 150 is configured to output presentation contents presented by the support system 100. The output unit 150 can include, for example, a display, a speaker, and the like.

Next, a main function of the support system 100 will be described.

The storage unit 120 is configured to store various data such as the use state data D1 on the use state of the medical device during the operation, the target lesion data D2 on the target lesion of the patient during the operation, and other data D3. In addition, the storage unit 120 is configured to store a support program for providing a support method according to the present embodiment disclosed here.

As illustrated in FIG. 3B, the CPU 110 functions as a data acquisition unit 111, a learning unit 112, and a presentation unit 113 by executing the support program stored in the storage unit 120.

The data acquisition unit 111 and each data will be described.

The data acquisition unit 111 is configured to acquire the use state data D1, the target lesion data D2, and other data D3.

For example, as illustrated in FIG. 4A, the use state data D1 can include data on a sampling time at which data has been acquired at the time of the operation, an operation policy, a medical device in use, an elapsed time from the start of the operation, and a progress state of the medical device.

The data acquisition unit 111 can acquire the use state data D1, for example, automatically, regularly (i.e., at set intervals), or irregularly (i.e., irregular intervals) during the operation. The use state data D1 can be transmitted directly or indirectly from various diagnosis devices (for example, a CT device, a catheter device for image diagnosis, and the like) used during the operation through an input operation by a health care worker such as a nurse. The acquired use state data D1 can be, for example, updated in real time, every time the data is acquired.

The operation policy can include, for example, a policy determined at a conference or the like held prior to the operation at the time of the start of the operation or data on decisions determined by a doctor who is in charge of the operation before the operation. When the policy is changed during the operation, the changed content is acquired as sample data. The policy can include, for example, data such as a type of the medical device to be used, a timing of switching the medical device, and an approach to a disease (for example, selection or change of antegrade/retrograde in an operation for a stenosed site of a lower-limb blood vessel). In addition, the progress state can include, for example, data such as an arrival state of the medical device to the target lesion and a progress state of a procedure of the target lesion using the medical device.

As illustrated in FIG. 4B, the target lesion data D2 can include, for example, data on a sampling time at which the data has been acquired at the time of the operation and a condition of the target lesion. The data acquisition unit 111 can acquire the target lesion data D2 automatically, regularly (i.e., at set intervals), or irregularly (i.e., at irregular intervals) together with the use state data D1 during the operation.

For example, when the disease to be operated is a coronary stenosis lesion or the like, the condition of the target lesion can include a degree of stenosis of the stenosed site and characteristics of the target lesion (such as a hardness of the blood vessel wall).

Other data D3 to be acquired from the data acquisition unit 111 can include, for example, the health care worker data D31 illustrated in FIG. 4C, the patient data D32 illustrated in FIG. 4D, the medical institution data D33 illustrated in FIG. 4E, and the prescription data D34 illustrated in FIG. 4F, and the medical cost data D35 illustrated in FIG. 4G.

As illustrated in FIG. 4C, the health care worker data D31 can include, for example, data on a medical institution name, a name of doctor scheduled to be in charge of the operation, a patient name, a disease name, an operating method to be adopted for the operation, and an operating time to be scheduled.

As illustrated in FIG. 4D, the patient data D32 can include, for example, data on a patient's identification ID (for example, data that can be acquired from My Number or the like), a patient name, address, age, a past operation history, a health condition, a name of current target lesion to be operated, and a condition of the target lesion. The data on the operation history, the health condition, and the condition of the target lesion can be acquired from, for example, an electronic medical record. For example, when the target lesion to be operated is a blood vessel, the data on the condition of the target lesion can include data on a running state (i.e., appearance) of the blood vessel. As the data on the running state of the blood vessel, a diagnostic image (imaging data, a CT image, a magnetic resonance imaging (MRI) image, or the like obtained from a catheter for image diagnosis) acquired by an examination performed prior to the operation using various medical devices can be used. The patient data D32 can also include data, which is obtained from the medical institution, on a past medical history, a family structure, and results of health examination (a height, a weight, and a blood pressure), and the like.

The patient data D32 may include, for example, data on genetic information of the patient. The genetic information may include not only the genetic information of the patient but also genetic information, for example, of a relative. The genetic information can include, for example, a DNA test result or the like. The genetic information can be used, for example, to determine whether a disease may be strongly affected by genetic factors when determining a disease of the patient.

As illustrated in FIG. 4E, the medical institution data D33 can include, for example, data on the medical institution such as a name, address, a medical treatment subject, the number of maintenance equipment such as beds and rescuers, a medical device, a clinical path, a policy, and the like. In addition, the medical device data can include, for example, data on what kind of medical device the medical institution holds, performance (specification) of the medical device held in the medical institution, and the like. In addition, the policy data can include data on an operation policy recommended by each medical institution, a medical device whose use is restricted at each medical institution, an educational policy such as training, and a medical policy such as priority medical care. In addition, the clinical path data can include, for example, a schedule table that summarizes a schedule from hospitalization to leaving hospital of a plurality of patients.

The medical institution data D33 can include, for example, data on a layout of the medical institution (data indicating a position and a distance of each equipment, a consulting room, an examination room, an operating room, a nurse station, a general ward, an intensive care unit (ICU), a high care unit (HCU), and the like). Further, the medical institution data D33 can include data on a congestion state of the medical institution. The data on the congestion state can include, for example, the congestion state of the medical institution within a certain distance from a patient's home (a congestion state related to an outpatient, a congestion state related to hospitalization, and the like). For example, when a patient visits a predetermined medical institution, the support system 100 can provide the patient with optimal transportation information (timetable, transfer guidance, and the like) based on data on traffic information and the congestion state, recommend a doctor with relatively excellent results in treatment for a particular disease, or present a medical institution in which such a doctor works. Further, the support system 100 may present the medical institution by means of transportation, and automatically perform a medical examination reservation or the like in accordance with an arrival time to the medical institution.

As illustrated in FIG. 4F, the prescription data D34 can include, for example, data on a patient's identification ID, a patient name, a prescription history A of a medicine prescribed at the medical institution, a prescription history B of a medicine prescribed at a pharmacy, and the like. The prescription history A can include, for example, data on a date and time of prescription, a type of medicine, a prescribed dose, a dosage form, and the like. In addition, the prescription history B can include data on a medicine actually prescribed to the patient at the pharmacy based on the prescription provided by the medical institution. The prescription history B can include, for example, data on a date and time of prescription, a type of medicine, a prescribed dose, a dosage form, and the like (prescription history and the like described in a medicine notebook). The medicine according to the present embodiment can include a so-called digital medicine equipped with a digital function (for example, a function of detecting biological information of a biological organ after taking the medicine and acquiring the information). For example, the information on the patient acquired from the digital medicine can be used for sharing with the medical institution, the patient, and the health care worker or monitoring a medicine-taking state of the patient.

As illustrated in FIG. 4G, the medical cost data D35 can include, for example, data on an operation name, an insurance cost recorded when the operation is performed, and a cost (sales price) of the medical device to be used in the operation.

Further, the other data D3 can include reuse data on the medical device and the medicine. The reuse data can include, for example, information on whether the medical device can be reused by performing cleaning or sterilization process. The medical device is, for example, a single-use medical device, but may be a medical device (component of a part of the medical device) other than the single-use medical device. In addition, the reuse data can include, for example, information on a remaining medicine. The remaining medicine can include, for example, information on whether a drug (for example, a liquid drug) stored in a predetermined dose in a container such as a bottle can be used for a plurality of patients. For example, when a drug stored in a particular container can be administered to a patient and a drug stored in a similar container can be administered to another patient, the drug is treated as reusable.

Note that the reuse data can be acquired in real time from, for example, a hospital information system of a medical institution having a medical device or medicine to be reused.

For example, the other data D3 (health care worker data D31, patient data D32, medical institution data D33, prescription data D34, medical cost data D35) is stored in the storage unit 120 prior to the operation performed on the patient.

The data acquisition unit 111 can acquire, for example, medical data as other information useful for supporting health care workers (doctor, nurse, and the like). Examples of the medical data include disease data on a diseases (disease name, symptoms, necessity of medical treatment, and the like), treatment data on a treatment (treatment method, period required for treatment, necessary equipment and drugs, and wholesale prices of the necessary equipment and drugs, and the like), usage example data on a method for using the medical device, and the like. For example, the data acquisition unit 111 can acquire the medical data from the Internet or electronic data of a medical specialty book captured by a scanner or the like.

Further, the data acquisition unit 111 can acquire, for example, via the Internet or the like, environmental information (weather, temperature, humidity, sunshine duration, population in specific region, main family structure in specific region, age group in specific region, data on disease epidemic in specific region, and the like) around the medical institution where the operation is performed. Further, the data acquisition unit 111 can also acquire, for example, data on traffic information in a specific region. The data on traffic information can include, for example, a distance from the patient's home to the medical institution, and a type of available transportation (for example, bus or train).

Next, the learning unit 112 will be described.

The learning unit 112 is configured to perform machine learning using the use state data D1, the target lesion data D2, and other data D3. In this specification, "machine learning" refers to analyzing input data using an algorithm, extracting useful rules and determination criteria from the analyzed result, and developing the algorithm.

The support system 100 according to the present embodiment performs machine learning based on the use state data D1 and the target lesion data D2 obtained during the operation to support the doctor while the doctor is performing the operation, and presents the operation policy recommended in real time.

Specifically, the presentation unit 113 of the support system 100 is presented, in real time, the operation policy recommended at this point in time in consideration of the progress of the operation, when a request is made by a doctor or a nurse during the operation, or when it is recommended to present the result of the machine learning even without the request. In addition, when the recommended operation policy is presented, the presentation unit 113 presents a presentation basis that led to the presentation together with the presentation contents. When there are a plurality of bases, the presentation unit 113 presents the plurality of bases. The presentation unit 113 presents the basis that led to the presentation of the operation policy together with the operation policy, such that a doctor, a nurse, or the like can adopt the presentation contents with satisfaction. Note that in a method for presenting the basis, a relationship between data may be represented using a graph or table, or an event to be a cause of the basis may be specifically represented with a number such as a contribution rate.

Figures 5, 6:
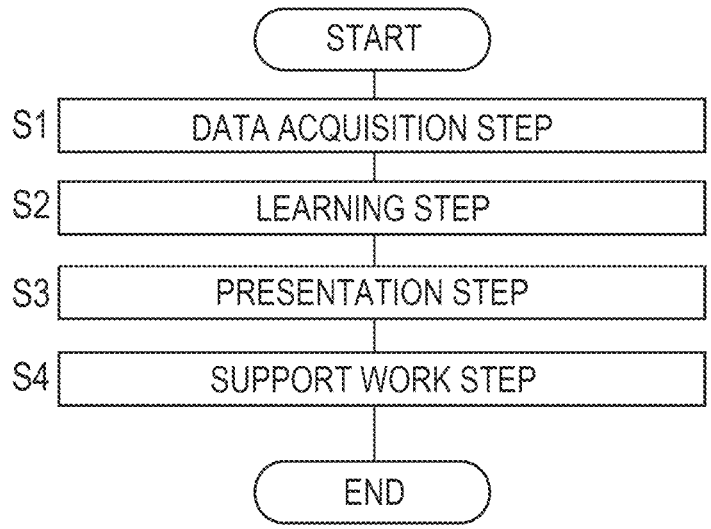
FIG. 5 is a flowchart illustrating a support method according to the present embodiment disclosed here.
FIG. 6 is a diagram illustrating presentation contents and a presentation basis shown by the support system according to the present embodiment disclosed here.

FIGS. 5 and 6 are diagrams for explaining the support method according to the present embodiment disclosed here. Hereinafter, the support method according to the present embodiment will be described with reference to FIGS. 5 and 6.

When briefly described with reference to FIG. 5, the support method includes a data acquisition step (S1) of acquiring the use state data D1 and the target lesion data D2, a learning step (S2) of performing machine learning using the use state data D1 and the target lesion data D2, a presentation step (S3) of presenting the recommended operation policy based on a result of the machine learning, and a support work step (S4) of performing a support work for a medical action. Hereinafter, each step will be described.

Note that a machine learning algorithm is generally classified into a supervised learning algorithm, an unsupervised learning algorithm, a reinforcement learning algorithm, and the like. The supervised learning algorithm provides a set of input data and result data to the learning unit 112 and performs the machine learning. The unsupervised learning algorithm provides only a large amount of the input data to the learning unit 112 and performs the machine learning. The reinforcement learning algorithm changes an environment based on the solution output from the algorithm, and makes corrections based on a reward of how correct the output solution is. As the machine learning algorithm of the learning unit 112, for example, the supervised learning algorithm, the unsupervised learning algorithm, the reinforcement learning algorithm, a combination of the supervised learning algorithm, the unsupervised algorithm, and/or the reinforcement learning algorithm, or the like can be used.

First, the data acquisition step (S1) will be described.

In the data acquisition step (S1), the data acquisition unit 111 is configured to acquire the use state data D1 and the target lesion data D2 during the operation and allows the storage unit 120 to store the use state data D1 and the target lesion data D2.

Next, the learning step (S2) will be described.

In the learning step (S2), the learning unit 112 is configured to apply a predetermined learning algorithm based on each data D1 and D2 stored in the storage unit 120. For example, when the supervised learning algorithm is adopted, a known algorithm such as a least-squares method, linear regression, autoregression, or a neural network can be applied. The other data D3 is used for the machine learning together with the use state data D1 and the target lesion data D2, if necessary.

The learning unit 112 is configured to predict, for example, an operation (behavior) currently performed by the doctor using the learning algorithm, and predicts how the operation will proceed and what treatment results will be obtained as a result. In addition, the learning unit also predicts the next operation performed by the doctor and the result of the next operation performed by the doctor.

Further, the learning unit 112 can perform the machine learning on information contributed to determination of reuse of the medical device based on information related to the medical device used in the operation such as whether the medical device can be reused, and when the medical device can be reused, which method (cleaning or sterilization method) can be adopted to reuse the medical device and which component of the medical device can be reused. Similarly, the learning unit 112 can perform the machine learning on information contributed to determination of reuse of the medicine based on information related to the medicine used in the operation such as whether the medicine can be reused, and which method (preservation method of the medicine or providing method to the patient) can be adopted to reuse the medicine when the medicine can be reused. The presentation unit 113 can provide information on reuse of the medical device or the medicine in the medical institution by presenting a learning result of the machine learning described above. The medical institution can effectively reduce medical expenses by acquiring or sharing the learning result regarding the reuse between the medical institution and a specific medical institution or a plurality of medical institutions.

Next, the presentation step (S3) will be described.

As illustrated in FIG. 6, the presentation unit 113 is configured to present a learning result of the learning unit, for example. In addition, the presentation unit 113 presents the presentation basis together with the presentation contents. Note that the presentation contents and the presentation basis can be presented, for example, on a display or the like of the output unit 150 (see FIG. 1) included in the working device.

An example of the presentation content and the presentation basis will be described with reference to FIG. 6.

The presentation content presented by the support system 100 can include an operation policy. The operation policy can include, for example, a change in a medical device, a change in an operative strategy, and the like. In addition, the support system 100 presents support works necessary for the doctor or nurse in addition to the operation policy. The support work can include, for example, an adjustment of an contrast area while the doctor is performing the operation (change in imaging range to be narrow, change in an imaging range to be wide, change in imaging angle for the target blood vessel, and the like), an adjustment of a position (height, longitudinal direction) or attitude of an operating table used in the operation, a guidance (guidance by image or voice) for a next step of an operation to be performed by the doctor, a provision of the support work (transfer the medical device, a work to wipe the doctor's sweat), and other works.

When the support work is presented, the support system 100 operates the support system 100 itself, and automatically performs the support work. Note that the support system 100 may start performing the support work after receiving an input from the doctor or the nurse without automatically performing the support work, or may merely present to encourage the performance to the nurse or the like. In addition, for example, when the support system 100 automatically performs the support work, the support system 100 may select and perform only those having a relatively high recommendation degree (advantage) to be performed among the presented support works.

For example, the support system 100 adjusts the contrast area, such that the doctor can capture an image of only an area necessary for the operation. Therefore, an exposure dose of the patient can be reduced. In addition, the support system 100 detects a posture of a surgeon to adjust a position or attitude of the operating table, such that the doctor can easily perform the operation. In addition, for example, if the support system 100 provides the guidance for the next step when an unexpected situation occurs, the doctor can proceed with the operation in a relatively calm state without falling into a panic state. In addition, the support system 100 transfers the medical device, such that the doctor can perform the operation relatively smoothly.

The doctor selects the operation policy based on a content presented by the support system 100 and proceeds with the operation. The support system 100 can be configured to receive various new data (use state data D1 and target lesion data D2) acquired during the operation in accordance with the operation policy selected by the doctor, and appropriately presents a new operation policy during the operation. In addition, the learning unit 112 can perform the machine learning using update data and update a learning model. In addition, various data obtained from the operation performed by the doctor can be stored as new data and used for the next operation.

Figure 7:
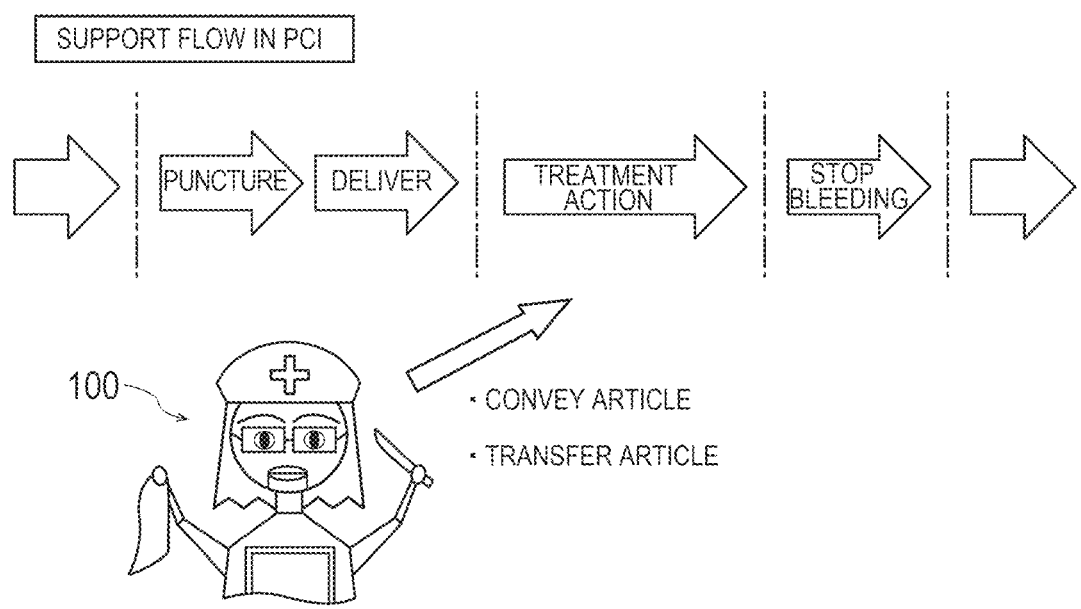
FIG. 7 is a diagram illustrating an example of a support flow in a percutaneous coronary intervention (PCI) surgery.

FIG. 7 illustrates an example of a support flow of the support system 100 in a percutaneous coronary intervention (PCI) procedure. The medical action during the operation supported by the support system 100 can include, for example, various procedures performed prior to the treatment action and various procedures performed after the treatment action, in addition to a treatment action using a balloon catheter, a stent, or the like. As described above, the support system 100 can perform the support with a total flow of the entire predetermined procedure. Examples of the support provided by the support system 100 in the support flow illustrated in FIG. 7 can include various suggestions (for example, suggestion or operation policy and the like or suggestion of using device), work support (for example, delivery of articles, contact with external facilities, and the like) by the support system 100, and assistance in medical action performed by a surgeon. The medical action to be performed or the presentation content is not particularly limited as long as the support provided by the support system 100 can contribute as a support of the medical action during the operation. As an example, the support system 100 can support a puncturing work performed into a blood vessel from a patient's arm, hand, leg, or the like to form an access path, a work for delivering the medical device from a puncture site formed in a patient to a treatment site, or the like. The support system 100 can also support, for example, a hemostatic work to stop the bleeding of the puncture site formed in the patient. Furthermore, the support system 100 can move an article (for example, a medical device or the like) in an operating room, transfer and receive the article to a doctor or a nurse, and support the delivery of a missing article in the operating room from a room other than the operating room or external facilities (for example, another hospital located nearby), while the medical action is performing.

As described above, the support system according to the present embodiment can include the data acquisition unit 111 that acquires, during the operation, the use state data D1 on the use state of the medical device during the operation and the target lesion data D2 on the target lesion of the patient during the operation, the learning unit 112 that performs machine learning using the use state data D1 and the target lesion data D2, and the presentation unit 113 that presents a recommended operation policy based on the result of the machine learning.

As described above, the support system 100 presents the recommended operation policy based on the result of the machine learning. Since a doctor can receive the presentation of the operation policy in real time during the operation, it is possible to adopt an objective and valid operation policy that does not depend only on the doctor's own decision.

The use state data D1 can include progress state data on a progress state of the medical device, and the target lesion data D2 can include target lesion condition data on a condition of the target lesion. Therefore, the support system 100 can present a higher objectivity and valid operation policy, and thus can suitably improve a success rate of the operation.

Further, the support system 100 can include a working device that performs a support work for a medical action. The learning unit 112 learns a recommended support work. Thus, the working device can perform the adjustment of the contrast area, the adjustment of the operating table, the guidance for the next step in the operation, the provision of an auxiliary work of the health care worker, and the combination of the adjustment of the contrast area, the adjustment of the operating table, the guidance for the next step, and/or the provision of the auxiliary work of the health care worker, which are at least included in the learning result of the learning unit 112. Therefore, the support system 100 can significantly reduce a workload on the doctor and the nurse.

When the target lesion of the patient is a blood vessel, the support system 100 can present an operation policy recommended in an operation on the blood vessel (for example, PCI or the like) by the presentation unit 113. Therefore, the doctor or the like can obtain a relatively higher objectivity and valid operation policy when performing the operation on the blood vessel.

In addition, the presentation unit 113 presents the presentation basis together with the presentation contents. Therefore, the doctor can adopt the presentation content with relative satisfaction.

Further, the support method according to the present embodiment includes the data acquisition step (S1) of acquiring, during the operation, the use state data D1 on the use state of the medical device during the operation and the target lesion data D2 on the target lesion of the patient during the operation, the learning step (S2) of performing the machine learning using the use state data D1 and the target lesion data D2, and the presentation step (S3) of presenting the recommended operation policy based on the result of the machine learning. For this reason, the doctor can receive the presentation of the operation policy in real time during the operation, and thus it is possible to adopt an objective and valid operation policy that does not depend only on the doctor's own decision.

Further, the support program according to the present embodiment causing a computer to execute a data acquisition step (S1) of acquiring, during the operation, the use state data D1 on the use state of the medical device during the operation and the target lesion data D2 on the target lesion of the patient during the operation, the learning step (S2) of performing the machine learning using the use state data D1 and the target lesion data D2, and the presentation step (S3) of presenting the recommended operation policy based on the result of the machine learning. For this reason, the doctor can receive the presentation of the operation policy in real time during the operation, and thus it is possible to adopt an objective and valid operation policy that does not depend only on the doctor's own decision.

As described above, the support system, the support method, and the support program according to the present disclosure have been described through the embodiment. However, the present disclosure is not limited to only each configuration described in the specification, and can be appropriately changed based on the scope of the description in the claims.

For example, the support system, the support method, and the support program according to the above-described embodiment may share the acquired data and the presentation contents by the plurality of medical institutions, or use the acquired data and the presentation content by only the single medical institution.

Further, the data used in the machine learning according to the present disclosure only needs to include at least the use state data on the use state of the medical device and the target lesion data on the target lesion of the patient. In addition, a content to be presented needs to include at least an operation policy.

Further, the support system, the support method, and the support program according to the present disclosure can widely include the medical device used during the operation, and examples of the medical device include a catheter device, a guidewire, and the like. In addition, the target lesion to which the present disclosure is applied, the contents of the operation, and the like are not particularly limited, and a site to be operated in the patient's biological organ and various operation policies that can be adopted for each target lesion can be widely presented.

Means and methods for executing various processing in the support system according to the embodiment described above can be realized by either one of a dedicated hardware circuit or a programmed computer. In addition, the support program may be provided by, for example, a computer-readable recording medium such as a compact disc read only memory (CD-ROM) or may be provided online via a network such as the Internet. In this case, the program recorded in the computer-readable recording medium is normally transferred to and stored in a storage unit such as a hard disk. In addition, the support program may be provided as standalone application software.

The detailed description above describes embodiments of a support system, a support method, and a support program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A support system configured to support a medical action during an operation, the system comprising:
   a data acquisition unit configured to acquire, during the operation, use state data on a use state of a medical device during the operation, and target lesion data on a target lesion of a patient during the operation;
   a learning unit configured to perform machine learning using the use state data and the target lesion data; and
   a presentation unit configured to present a recommended operation policy based on a result of the machine learning.

2. The support system according to claim 1, wherein the use state data includes progress state data on a progress state of the medical device, and the target lesion data includes target lesion condition data on a condition of the target lesion.

3. The support system according to claim 1, further comprising:
a working device configured to perform support work for the medical action;
wherein the learning unit is configured to perform machine learning on the recommended support work; and
the working device is configured to perform an adjustment of a contrast area, an adjustment of an operating table, a guidance for a next step in the operation, a provision of an auxiliary work of a health care worker, and a combination of the contrast area, the adjustment of the operating table, the guidance for the next step in the operation, and/or the provision of the auxiliary work of the health care worker, which are at least included in a learning result of the learning unit.

4. The support system according to claim 1,
wherein the target lesion is a blood vessel of the patient; and
the presentation unit is configured to present an operation policy recommended in an operation on the blood vessel.

5. The support system according to claim 1, wherein the presentation unit is configured to present a presentation basis together with a presentation content.

6. The support system according to claim 1, wherein the machine learning is a supervised learning algorithm, an unsupervised learning algorithm, a reinforcement learning algorithm, or a combination of the supervised learning algorithm, the unsupervised algorithm, and/or the reinforcement learning algorithm.

7. The support system according to claim 1, wherein the presentation unit includes a display to present the recommended operation policy.

8. The support system according to claim 1, wherein the data acquisition unit is configured to acquire the use state data at one or more of the following: automatically, at regularly set intervals, and/or at irregular set intervals during the operation.

9. The support system according to claim 1, wherein
the use state data is transmitted directly from each of the diagnostic devices used during the operation through an input operation by a health care worker, and
the acquired use state data is updated in real time, every time the data is acquired.

10. A support method configured to support a medical action during an operation, the method comprising:
acquiring, during the operation, use state data on a use state of a medical device during the operation, and target lesion data on a target lesion of a patient during the operation;
performing machine learning using the use state data and the target lesion data; and
presenting a recommended operation policy based on a result of the machine learning on display of a presentation unit.

11. The support method according to claim 10, wherein the use state data includes progress state data on a progress state of the medical device, and the target lesion data includes target lesion condition data on a condition of the target lesion.

12. The support method according to claim 10, further comprising:

performing support work for the medical action with a working device;
performing machine learning on the recommended support work; and
performing an adjustment of a contrast area, an adjustment of an operating table, a guidance for a next step in the operation, a provision of an auxiliary work of a health care worker, and a combination of the contrast area, the adjustment of the operating table, the guidance for the next step in the operation, and/or the provision of the auxiliary work of the health care worker, which are at least included in a learning result of the learning unit with the working device.

13. The support method according to claim 10, wherein the target lesion is a blood vessel of the patient, the method further comprising:
presenting an operation policy recommended in an operation on the blood vessel.

14. The support method according to claim 10, further comprising:
presenting a presentation basis together with a presentation content on the display of the presentation unit.

15. The support method according to claim 10, wherein the machine learning is a supervised learning algorithm, an unsupervised learning algorithm, a reinforcement learning algorithm, or a combination of the supervised learning algorithm, the unsupervised algorithm, and/or the reinforcement learning algorithm.

16. The support method according to claim 10, further comprising:
acquiring the use state data at one or more of the following:
automatically, at regularly set intervals, and/or at irregularly set intervals during the operation.

17. The support method according to claim 10, further comprising:
transmitting directly the use state data from each of the diagnostic devices used during the operation through an input operation by a health care worker; and
updating in real time the acquired use state data, every time the data is acquired.

18. A non-transitory computer readable medium (CRM) storing computer program code executed by a computer processor that executes a process of supporting a medical action during an operation, the process comprising:
acquiring, during the operation, use state data on a use state of a medical device during the operation, and target lesion data on a target lesion of a patient during the operation;
performing machine learning using the use state data and the target lesion data; and
presenting a recommended operation policy based on a result of the machine learning.

19. The computer readable medium according to claim 18, wherein the use state data includes progress state data on a progress state of the medical device, and the target lesion data includes target lesion condition data on a condition of the target lesion.

20. The computer readable medium according to claim 18, further comprising:
performing support work for the medical action with a working device;
performing machine learning on the recommended support work; and
performing an adjustment of a contrast area, an adjustment of an operating table, a guidance for a next step in the operation, a provision of an auxiliary work of a health care worker, and a combination of the contrast area, the adjustment of the operating table, the guidance for the next step in the operation, and/or the provision of the auxiliary work of the health care worker, which are at least included in a learning result of the learning unit with the working device.

* * * * *